United States Patent
Takenaka et al.

(10) Patent No.: US 9,409,926 B2
(45) Date of Patent: Aug. 9, 2016

(54) CHIRAL 4-BORONOPHENYLALANINE (BPA) DERIVATIVE AND METHOD FOR PRODUCING SAME, AND METHOD FOR PRODUCING $^{18}$F-LABELED BPA USING SAID DERIVATIVE

(71) Applicants: Osaka Prefecture University Public Corporation, Sakai-Shi, Osaka (JP); Stella Pharma Corporation, Chuo-ku, Osaka-Shi, Osaka (JP)

(72) Inventors: Hiroshi Takenaka, Osaka (JP); Yoichiro Ohta, Osaka (JP); Yusuke Taguchi, Osaka (JP); Sayuri Ueda, Osaka (JP); Yuko Ishino, Osaka (JP); Hideki Nakashima, Osaka (JP); Kohki Uehara, Osaka (JP); Mitsunori Kirihata, Sakai (JP)

(73) Assignee: STELLA PHARMA CORPORATION; OSAKA PREFECTURE UNIVERSITY PUBLIC CORPORATION, Osaka (JP)

( * ) Notice: Subject to any disclaimer, the term of this patent is extended or adjusted under 35 U.S.C. 154(b) by 0 days.

(21) Appl. No.: 14/435,678

(22) PCT Filed: Oct. 8, 2013

(86) PCT No.: PCT/JP2013/077366
§ 371 (c)(1),
(2) Date: Apr. 14, 2015

(87) PCT Pub. No.: WO2014/061508
PCT Pub. Date: Apr. 24, 2014

(65) Prior Publication Data
US 2015/0329564 A1    Nov. 19, 2015

(30) Foreign Application Priority Data
Oct. 15, 2012    (JP) ................................. 2012-228053

(51) Int. Cl.
| | | |
|---|---|---|
| *C07F 5/02* | (2006.01) | |
| *C07C 229/08* | (2006.01) | |
| *C07F 5/04* | (2006.01) | |
| *C07C 229/36* | (2006.01) | |
| *C07B 59/00* | (2006.01) | |
| *C07C 271/22* | (2006.01) | |
| *C07C 251/24* | (2006.01) | |

(52) U.S. Cl.
CPC .............. *C07F 5/025* (2013.01); *C07B 59/001* (2013.01); *C07C 229/08* (2013.01); *C07C 229/36* (2013.01); *C07C 251/24* (2013.01); *C07C 271/22* (2013.01); *C07F 5/027* (2013.01); *C07F 5/04* (2013.01); *Y02P 20/55* (2015.11)

(58) Field of Classification Search
CPC .................................. C07F 5/025; C07F 5/027
See application file for complete search history.

(56) References Cited

FOREIGN PATENT DOCUMENTS

| JP | 2000 212185 A | 8/2000 |
|---|---|---|
| JP | 2008-214319 A | 9/2008 |

OTHER PUBLICATIONS

Suominen, 2001, Frontiers in Neutron Capture Therapy, p. 839-841.*
Endo, Yasuyuki, et al., Role of the hydrophobic moiety of tumor promoters. Synthesis and Activity of 9-Alkylated Benzolactams, Chem. Pharm. Bull, 44(5), p. 1138-1140, 1996.
Ishiwata, Kiichi, et al., Synthesis and Radiation Dosimetry of 4-Borono-2-[18F] Fluoro-D, L-phenylalanine; a Target Compound for PET and Boron Neutron Capture Therapy. Appl. Radiat. Isot., vol. 42, No. 4, 325-328, 1991.
McAllister, Laura A., et al., A General Strategy for the Synthesis of Cyclic N-Aryl Hydroxamic Acids via Partial Nitro Group Reduction, Journal of Organic Chemistry, 76(9), p. 3484-3497, 2011.
Meyer, Falco-Magnus, et al., Functionalization of Aromatic Amino Acids via Direct C—H Activation: Generation of Versatile Building Blocks for Accessing Novel Peptide Space, Organic Letters, 12(17), p. 3870-3873, 2010.
Porcari, P. et al., In vivo 19F MR imaging and spectroscopy for the BNCT optimization, Applied Radiation and Isotopes, 67, S365-368, 2009.
Tuttle, Jamison B., et al., Synthesis of ortho-substituted nitroaromatics via improved Negishi coupling conditions, Tetrahedron Letters, 52(41), p. 5211-5213, 2011.
Vahatalo, Jyrki K., et al., Synthesis of 4-dihydroxyboryl-2-[18F] fluorophenylalanine with relatively high-specific activity. J. Labelled Compounds and Radiopharmaceuticals, 45, p. 697-704, 2002.

(Continued)

*Primary Examiner* — Michael Barker
*Assistant Examiner* — Karen Cheng
(74) *Attorney, Agent, or Firm* — Knobbe Martens Olson & Bear LLP

(57) ABSTRACT

Provided are: a novel chiral 4-boronophenylalanine (BPA) derivative; a method for producing the derivative; and a method for producing $^{18}$F-2-fluoro-4-borono-L-phenylalanine ($^{18}$F-labeled BPA; 18F-BPA) using the derivative. A compound represented by formula (1) is prepared. In the formula, R represents $BR^3R^4$, $BX_3^-$ or $BX_3^-M^+$ (wherein X represents a halogen atom, and $M^+$ represents a monovalent monoatomic cation, a polyatomic cation or a complex cation); $R_1$ represents a hydrogen atom or a protecting group PG1; $R_2$ represents a hydrogen atom or a protecting group PG2; $R_3$ and $R_4$ independently represent OH, or $R^3$, $R^4$ and B together form a ring that serves as a protecting group; and Y represents a halogen atom, $NO_2$, $NH_2$, $Sn(R^6)_3$, N=N—$NR^7R^8$, $OSO_2R^9$, $NR^{10}R^{11}$, a substituted or unsubstituted phenyliodo group or a substituted or unsubstituted heterocyclic iodo group. The compound is reacted with a fluorination reagent to prepare $^{18}$F-labeled BPA.

7 Claims, No Drawings

(56) References Cited

OTHER PUBLICATIONS

International Search Report for International App. No. PCT/JP2013/077366 issued Dec. 24, 2013.
Suominen, M. et al. "Synthetic Approaches to a Novel Iodinated Analogue of BPA." *Frontiers in Neutron Capture Therapy.* vol. 2, 2014, 839-41.
Shi, Zhi-Cai, et al. "Modulation of Peripheral Serotonin Levels by Novel Tryptophan Hydroxylase Inhibitors for the Potential Treatment of Functional Gastrointestinal Disorders." *J. Med. Chem*(2008): 1-63.
A.H. Liao, F.I. Chou, Y.C. Kuo, H.W. Chen, J.J. Kai, C.W. Chang, F.D. Chen, J.J. Hwang, Biodistribution of phenylboric acid derivative entrapped lipiodol and 4-borono-2-$^{18}$F-fluoro-L-phenylalanine-fructose in GP7TB liver tumor bearing rats for BNCT, *Applied Radiation and Isotopes*, vol. 68, Issue 3, Mar. 2010, 422-426.
Porcari, Paola; et al. Multi-nuclear MRS and $^{19}$F MRI of $^{19}$F-labelled and $^{10}$B-enriched p-boronophenylalanine-fructose Complex to Optimize Boron Neutron Capture Therapy: Phantom Studies at High Magnetic Fields; *Physics in Medicine and Biology*, vol. 51, No. 12, (2006): 3141-3154.
Mccord, T. J., Crawford, C. P., Rabon, J. A., Gage, L. D., Winter, J. M. and Davis, A. L. (1982), A comparative study of the rearrangement of some 6- and 7-halo-substituted 3-amino-3,4-dihydro-1-hydroxycarbostyrils in concentrated hydrohalic acids. *Journal of Heterocyclic Chemistry*, vol. 19, No. 2, 401-406.
Davis, A.L. et al., "Synthesis and Antibacterial Activities of Some Chloro Analogs of 3-Amino-3,4-dihydro-1-hydroxycarbostyril", *Journal of Medicinal Chemistry* 1975, vol. 18, No. 7, 752-755.
Al-Darwich, M.J. et al., Enantioselective syntheses of no-carrier-added (n. c.a.) (s)-4-chloro-2-[$^{18}$F] fluorophenylalanine and (S)-(α-methyl)-4-chloro-2-[$^{18}$F]fluorophenylalanine, Journal of Fluorine Chemistry, vol. 80, No. 2, Oct. 1996, pp. 117-124.
Kabalka G.W. et al., "Synthesis of 4-borono-2-fluorophenylalanine", Organic Preparations and Procedures International, vol. 32, No. 3, 2000, 290-293.
Kubota, R. et al. "Cellular Accumulation of $^{18}$F-Labelled Boronophenylalanine depending on DNA synthesis and melanin incorporation: a double-tracer microautoradiographic study of B16 melanomas in vivo." *British Journal of Cancer*, vol. 67, No. 4, 1993, 701-705.
Supplementary European Search Report for International App. No. PCT/JP2013077366 issued Apr. 6, 2016.

* cited by examiner

CHIRAL 4-BORONOPHENYLALANINE (BPA) DERIVATIVE AND METHOD FOR PRODUCING SAME, AND METHOD FOR PRODUCING $^{18}$F-LABELED BPA USING SAID DERIVATIVE

This application is the U.S. National Phase under 35 U.S.C. §371 of International Application No. PCT/JP2013/077366, filed Oct. 8, 2013, designating the U.S., and published in Japanese as WO 2014/061508 on Apr. 24, 2014, which claims priority to Japanese Patent Application No. 2012-228053, filed Oct. 15 2012.

TECHNICAL FIELD

The present invention relates to a novel chiral 4-boronophenylalanine (BPA) derivative, a method for producing the derivative, and a method for producing $^{18}$F-labeled BPA ($^{18}$F-2-fluoro-4-borono-L-phenylalanine: $^{18}$F-BPA), using the derivative.

BACKGROUND ART

At present, attention has been paid to positron emission tomography (PET) as a technique that is high in sensitivity to be excellent in quantitatively determining performance and can form images easily in light of a principle thereof. This technique has widely been used. The half value period of PET diagnostic reagents (tracers) used for diagnoses is short, and the tracers are each administrated in a fine amount so that any living body is hardly exposed to radiation based thereon. Therefore, this inspecting method is a low invasive inspecting method, thus is greatly advantageous to PET. Furthermore, PET is highly sensitive even to tumors that are not easily determined by CT (computed tomography) or MRI (magnetic resonance imaging), and tumor tissues thereof can be evaluated according to images.

$^{18}$F-labeled BPA, in which a $^{18}$F-fluorine atom is introduced into BPA, which is a boronated amino acid used as a boron reagent for BNCT (boron neutron capture therapy), was developed as a molecular probe for PET by Ishiwata in 1991 (Non-Patent Document 1). Thereafter, a PET inspection with the use of $^{18}$F-labeled BPA using the present probe has been an important technique for supporting BNCT. In other words, in clinical and research spots, a $^{18}$F-BPA PET image obtained by measuring a subject beforehand can give data on an internal accumulation distribution of BPA, the ratio of tumor tissues/normal tissues (the T/N ratio) and others. On the basis of these data, curative effects of BNCT are beforehand assumed and then a research or therapeutic plan can be drawn up.

In Ishiwata's synthesis method, BPA is directly fluorinated to prepare $^{18}$F-labeled BPA, and $^{18}$F$^+$ is used as an electrophilic reagent. From deuterium (D) and neon (Ne) accelerated by a cyclotron, $^{18}$F gas is prepared, and then passed through a column filled with sodium acetate to convert the gas to $CH_3COO^{-18}F^+$. Thereafter, a solution of BPA in trifluoroacetic acid is bubbled by the introduction of this conversion-obtained compound into the solution. In this way, the synthesis of the target $^{18}$F-labeled BPA is attained.

As another method for synthesizing $^{18}$F-labeled BPA, Vahatalo et al. suggest a method in which such a conventional method is partially improved (Non-Patent Document 2). This method is a method of using $H^{18}F$, which can be obtained in a larger quantity, to attain the synthesis via $CH_3^{18}F$ as an intermediate of $^{18}F_2$. By causing $CH_3I$ to react with $H^{18}F$, which is obtained through the radiation of protons to $H_2^{18}O$ [through $^{18}O$ (p,n)$^{18}F$ reaction], $CH_3^{18}F$ is once synthesized. The resultant compound $CH_3^{18}F$ is discharged to disassociate its C—F bonds to prepare $^{18}F_2$. This compound is used to synthesize $^{18}$F-labeled BPA, equivalently to Ishiwata's synthesis method.

PRIOR ART DOCUMENTS

Non-Patent Documents

Non-Patent Document 1: Appl. Radiat. Isot., 42, 325, 1991
Non-Patent Document 2: J. Label. Compd. Radiopharm., 45, 697, 2002

SUMMARY OF THE INVENTION

Problems to be Solved by the Invention

However, the $^{18}$F-labeled BPA species obtained by the conventional synthesis method according to Ishiwata et al. is low in specific radioactivity and further extremely small in yield. Even by the improved method, the yield is still small although the specific radioactivity of the resultant $^{18}$F-labeled BPA species is heightened.

One of the objectives of the present invention is to provide a novel BPA derivative that can be an intermediate for synthesizing 18F-labeled BPA.

Another objective of the present invention is to provide a method for producing such a novel BPA derivative, and a method for producing $^{18}$F-labeled BPA, using this derivative.

Means for Solving the Problems

In order to solve the above-mentioned problems, the inventors have made eager investigations to find out a novel method for synthesizing $^{18}$F-labeled BPA. Thus, the present invention has been achieved.

Accordingly, the present invention relates to a compound represented by the following formula:

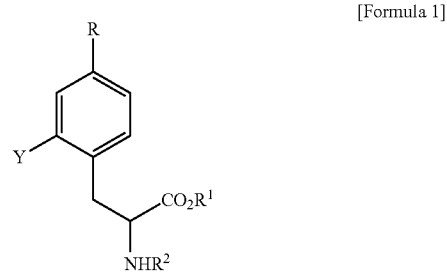

[Formula 1]

where R represents $BR^3R^4$, $BX_3^-$, or $BX_3^-M^+$ (X represents halogen; $M^+$ represents monovalent monoatomic cation, polyatomic cation, or complex cation); $R^1$ represents hydrogen or protecting group $PG^1$; $R^2$ represents hydrogen or protecting group $PG^2$; $R^3$ and $R^4$ each represents OH, or else $R^3$ and $R^4$ both combine with B (boron atom), to form a ring serving as protecting group for B; Y represents halogen, $NO_2$, $NH_2$, $Sn(R^6)_3$, $N=N-NR^7R^8$, $OSO_2R^9$, $NR^{10}R^{11}$, substituted or unsubstituted phenyl iodo group, or substituted or unsubstituted heterocyclic iodo group; $R^6$ represents alkyl group having 1 to 7 carbon atoms; $R^7$ and $R^8$, which may be the same or different, each represents hydrogen, alkyl group having 1 to 7 carbon atoms, halogen-substituted alkyl group having 1 to 7 carbon atoms, or optionally substituted phenyl group, or else $R^7$ and $R^8$ combine with N to form a 3- to 7-membered cyclic structure; $R^9$ represents alkyl group having 1 to 7 carbon atoms, halogen-substituted alkyl group having 1 to 7 carbon atoms, or optionally substituted phenyl group; and $R^{10}$ and $R^{11}$, which may be the same or different, each represents alkyl group having 1 to 7 carbon atoms, halogen-substituted alkyl group having 1 to 7 carbon atoms, or optionally substituted phenyl group, or else $R^{10}$ and $R^{11}$ combine with N to form a 3- to 7-membered cyclic structure; except that excluded herefrom is a situation in which the following conditions simultaneously exist: Y is F, $R^1$ and $R^2$ both represent hydrogen, and $R^3$ and $R^4$ both represent OH.

In this compound, it is preferred that Y represent I, F, $NO_2$, $NH_2$, $Sn(R^6)_3$, N=N—$NR^7R^8$, $OSO_2R^9$, $NR^{10}R^{11}$, $I^+R^{13}$, or $(R^{14-})I^+R^{13}$ wherein: $R^6$ represents methyl or n-butyl; $R^7$ and $R^8$ may be the same or different, and each represent hydrogen, methyl, ethyl, propyl, butyl, heptyl, trifluoromethyl or an optionally substituted phenyl group, or are combined with N to form aziridine, azetidine, pyrrolidine or piperidine; $R^9$ represents methyl, ethyl, propyl, butyl, heptyl, trifluoromethyl or an optionally substituted phenyl group; $R^{10}$ and $R^{11}$ may be the same or different, and each represent methyl, ethyl, propyl, butyl, heptyl, trifluoromethyl or an optionally substituted phenyl group, or are combined with N to form aziridine, azetidine, pyrrolidine, piperidine or homo-piperidine; $R^{13}$ represents a $C_{1-6}$-alkyl-substituted phenyl group, a $C_{1-6}$-alkoxy-substituted phenyl group or a phenyl group, or a 5- to 7-membered heterocyclic group having one or more atoms of N, S or O atoms; and $R^{14}$ represents a halogen, or a tetrafluoroborate, nitrate, triflate, sulfonyloxy, toluenesulfonyloxy, or perchlorate group.

In this compound, it is preferred that R represents $BR^3R^4$ wherein $R^3$ and $R^4$ each represent OH, or $R^3$ and $R^4$ are together combined with B to form the ring as the protecting group for B wherein the group to form the ring may be selected from the group consisting of pinacol, 3,3-dimethyl-1,3-propanediol, N-methyldiethanolamine, 1,8-diaminonaphthalene, N-methyliminodiacetic acid, 1,1,1-trishydroxymethylethane, and catechol; or R represents $BX_3^-$ or $BX_3M$ wherein X represents F, and $M^+$ represents an alkali metal ion, an ammonium ion, a tetraalkylammonium ion, a tetraarylammonoum ion, a tetraalkylphosphonium ion, a tetraarylphosphonium ion, or an imidazolium ion.

The compound of the present invention may be any one of the following compounds:
tert-butyl 2-(tert-butoxycarbonylamino)-3-(2-nitro-4-(4,4,5-tetramethyl-1,3,2-dioxaborolane-2-yl)phenyl)propanoate;
tert-butyl 3-(2-amino-4-(4,4,5,5-tetramethyl-1,3,2-dioxaborolane-2-yl)phenyl)-2-(tert-butoxycarbonylamino) propanoate;
tert-butyl 2-(tert-butyloxycarbonylamino)-3-(2-iodo-4-(4,4,5,5-tetramethyl-1,3,2-dioxaborolane-2-yl)phenyl)propanoate;
tert-butyl 2-(tert-butyloxycarbonylamino)-3-(4-(4,4,5,5-tetramethyl-1,3,2-dioxaborolane-2-yl)-2-(tri-n-butylstannyl)phenyl)propanoate;
tert-butyl 2-(tert-butoxycarbonylamino)-3-(2-fluoro-4-(4,4,5,5-tetramethyl-1,3,2-dioxaborolane-2-yl)phenyl)propanoate;
(2-(3-tert-butoxy-2-(tert-butoxycarbonylamino)-3-oxopropyl)-5-(4,4,5,5-tetramethyl-1,3,2-dioxaborane-2-yl)phenyl) (3-methoxyphenyl)iodonium tosylate;
tert-butyl 2-(tert-butyloxycarbonylamino)-3-(2-nitro-4-potassiumtrifluoroborylphenyl)propanoate; or
(2-(3-tert-butoxy-2-(tert-butoxycarbonylamino)-3-oxopropyl)-5-(potassiumtrifluoroborylphenyl)(3-methoxyphenyl)iodonium tosylate.

The present invention also relates to a method for producing a compound, including the step of using the following:

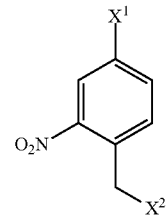

[Formula 2]

wherein $X^1$ and $X^2$ may be the same or different, and each represent a halogen, the produced compound being a compound represented by the following formula:

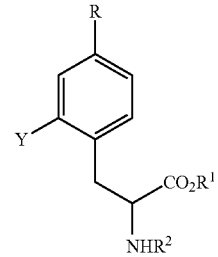

[Formula 3]

where R represents $BR^3R^4$, $BX_3^-$, or $BX_3^-M^+$ (X represents halogen; $M^+$ represents monovalent monoatomic cation, polyatomic cation, or complex cation); $R^1$ represents hydrogen or protecting group $PG^1$; $R^2$ represents hydrogen or protecting group $PG^2$; $R^3$ and $R^4$ each represents OH, or else $R^3$ and $R^4$ both combine with B (boron atom), to form a ring serving as protecting group for B; Y represents halogen, $NO_2$, $NH_2$, $Sn(R^6)_3$, N=N—$NR^7R^8$, $OSO_2R^9$, $NR^{10}R^{11}$, substituted or unsubstituted phenyl iodo group, or substituted or unsubstituted heterocyclic iodo group; $R^6$ represents alkyl group having 1 to 7 carbon atoms; $R^7$ and $R^8$, which may be the same or different, each represents hydrogen, alkyl group having 1 to 7 carbon atoms, halogen-substituted alkyl group having 1 to 7 carbon atoms, or optionally substituted phenyl group, or else $R^7$ and $R^8$ combine with N to form a 3- to 7-membered cyclic structure; $R^9$ represents alkyl group having 1 to 7 carbon atoms, halogen-substituted alkyl group having 1 to 7 carbon atoms, or optionally substituted phenyl group; and $R^{10}$ and $R^{11}$, which may be the same or different, each represents alkyl group having 1 to 7 carbon atoms, halogen-substituted alkyl group having 1 to 7 carbon atoms, or optionally substituted phenyl group, or else $R^{10}$ and $R^{11}$ combine with N to form a 3- to 7-membered cyclic structure; except that excluded herefrom is a situation in which the following conditions simultaneously exist: Y is F, $R^1$ and $R^2$ both represent hydrogen, and $R^3$ and $R^4$ both represent OH.

In the above-mentioned method, it is preferred to include the step of causing a compound represented by the following formula:

[Formula 4]

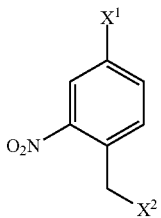

wherein X¹ and X² may be the same or different, and each represent a halogen, to react with one reagent selected from the group consisting of the following compounds in the presence of a basic catalyst:

a methyl ester of N-diphenylmethyleneglycine, an ethyl ester of N-diphenylmethyleneglycine, N-diphenylmethyleneglycine and a t-butyl ester of N-diphenylmethyleneglycine, and a benzyl ester of N-diphenylmethyleneglycine.

The present invention also relates to a method for producing $^{18}$F-labeled BPA, including the step of causing a compound represented by the following formula to react with a fluorinating reagent:

[Formula 5]

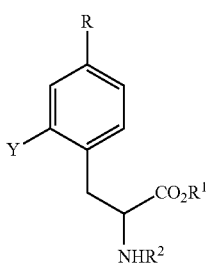

where R represents $BR^3R^4$, $BX_3^-$, or $BX_3^-M^+$ (X represents halogen; $M^+$ represents monovalent monoatomic cation, polyatomic cation, or complex cation); $R^1$ represents hydrogen or protecting group $PG^1$; $R^2$ represents hydrogen or protecting group $PG^2$; $R^3$ and $R^4$ each represents OH, or else $R^3$ and $R^4$ both combine with B, to form a ring serving as protecting group for B; Y represents halogen, $NO_2$, $NH_2$, $Sn(R^6)_3$, $N=N-NR^7R^8$, $OSO_2R^9$, $NR^{10}R^{11}$, substituted or unsubstituted phenyl iodo group, or substituted or unsubstituted heterocyclic iodo group; $R^6$ represents alkyl group having 1 to 7 carbon atoms; $R^7$ and $R^8$, which may be the same or different, each represents hydrogen, alkyl group having 1 to 7 carbon atoms, halogen-substituted alkyl group having 1 to 7 carbon atoms, or optionally substituted phenyl group, or else $R^7$ and $R^8$ combine with N to form a 3- to 7-membered cyclic structure; $R^9$ represents alkyl group having 1 to 7 carbon atoms, halogen-substituted alkyl group having 1 to 7 carbon atoms, or optionally substituted phenyl group; and $R^{10}$ and $R^{11}$, which may be the same or different, each represents alkyl group having 1 to 7 carbon atoms, halogen-substituted alkyl group having 1 to 7 carbon atoms, or optionally substituted phenyl group, or else $R^{10}$ and $R^{11}$ combine with N to form a 3- to 7-membered cyclic structure; except that excluded herefrom is a situation in which the following conditions simultaneously exist: Y is F, $R^1$ and $R^2$ both represent hydrogen, and $R^3$ and $R^4$ both represent OH.

The present invention also relates to a compound represented by the following formula:

[Formula 6]

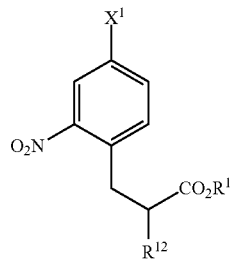

wherein $X^1$ represents a halogen; $R^1$ represents hydrogen or a protecting group $PG^1$; and $R^{12}$ represents $NH_2$, $NHPG^2$ wherein $PG^2$ is a protecting group, or aminomethylenediphenyl.

Effect of the Invention

The novel BPA derivative of the present invention is favorably usable, particularly, for producing $^{18}$F-labeled BPA.

MODE FOR CARRYING OUT THE INVENTION

The existing methods for synthesizing $^{18}$F-labeled BPA are methods for fluorinating BPA directly, and are attained, in particular, by conducting an electrophilic reaction by use of $^{18}$F as an electrophilic reagent. The inventors have paid attention to the following: in the step of preparing $^{18}$F$_2$ gas in a cyclotron, the step of using $F^+$ from the resultant $^{18}$F$_2$ gas, and some other step in an existing synthesis route as described above, problems are caused, respectively; and further $^{18}$F-labeled BPA obtained finally is lowered in specific radioactivity by the generation of a reaction product from contaminated $^{19}$F$_2$ molecules or by some other cause, and the $^{18}$F-labeled BPA quantity, usable for PET diagnoses, according to a single synthesis is a quantity for several persons. A novel method of the present invention for synthesizing $^{18}$F-labeled BPA is entirely different from the conventional methods, and is a synthesis method in which $^{18}$F anions are usable. This method makes a load onto the apparatus small, and makes it possible to synthesize $^{18}$F-labeled BPA to give a yield larger than the respective yields according to the conventional synthesis methods.

In the present invention, a novel BPA derivative is obtained. This novel BPA derivative is labeled easily and highly probable with $^{18}$F by a nucleophilic substitution reaction. Therefore, it is possible to yield $^{18}$F-labeled BPA easily and efficiently.

In the present invention, the BPA derivative is equivalent in meaning to a pinacol boride derivative represented by the following formula.

[Formula 7]

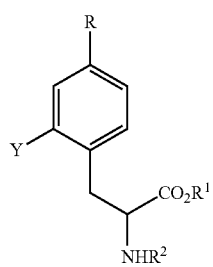

where R represents $BR^3R^4$, $BX_3^-$, or $BX_3^-M^+$ (X represents halogen; $M^+$ represents monovalent monoatomic cation, polyatomic cation, or complex cation); $R^1$ represents hydrogen or protecting group $PG^1$; $R^2$ represents hydrogen or protecting group $PG^2$; $R^3$ and $R^4$ each represents OH, or else $R^3$ and $R^4$ both combine with B, to form a ring serving as protecting group for B; Y represents halogen, $NO_2$, $NH_2$, $Sn(R^6)_3$, $N=N-NR^7R^8$, $OSO_2R^9$, $NR^{10}R^{11}$, substituted or unsubstituted phenyl iodo group, or substituted or unsubstituted heterocyclic iodo group; $R^6$ represents alkyl group having 1 to 7 carbon atoms; $R^7$ and $R^8$, which may be the same or different, each represents hydrogen, alkyl group having 1 to 7 carbon atoms, halogen-substituted alkyl group having 1 to 7 carbon atoms, or optionally substituted phenyl group, or else $R^7$ and $R^8$ combine with N to form a 3- to 7-membered cyclic structure; $R^9$ represents alkyl group having 1 to 7 carbon atoms, halogen-substituted alkyl group having 1 to 7 carbon atoms, or optionally substituted phenyl group; and $R^{10}$ and $R^{11}$, which may be the same or different, each represents alkyl group having 1 to 7 carbon atoms, halogen-substituted alkyl group having 1 to 7 carbon atoms, or optionally substituted phenyl group, or else $R^{10}$ and $R^{11}$ combine with N to form a 3- to 7-membered cyclic structure; except that excluded herefrom is a situation in which the following conditions simultaneously exist: Y is F, $R^1$ and $R^2$ both represent hydrogen, and $R^3$ and $R^4$ both represent OH.

In $BX_3^-$ or $BX_3^-M^+$ as R, Xs each represent a halogen, and are each in particular preferably F. $M^+$ represents a monovalent monoatomic cation, a polyatomic cation, or a complex cation. $M^+$ is in particular preferably an alkali metal ion such as $K^+$, $Na^+$ or $Li^+$, an ammonium ion, a tetraalkylammonium ion, a tetraarylammonoum ion, a tetraalkylphosphonium ion, a tetraarylphosphonium ion, or an imidazolium ion although $M^+$ is not limited. The word "alkyl" herein preferably represents a C1 to C6 alkyl although the alkyl is not limited. Particularly preferred examples of the tetraalkylammonium ion include a tetramethylammonium ion, a tetraethylammonium ion, a tetrabutylammonium ion, and a tetrapropylammonium ion. The word "aryl" herein preferably represents a substituted or unsubstituted phenyl group.

The wording "are combined with N to form a 3- to 7-membered cyclic structure" denotes a saturated or unsaturated ring having carbon and nitrogen.

In the present compound, Y preferably represents I, F, $NO_2$, $NH_2$, $Sn(R^6)_3$, $N=N-NR^7R^8$, $OSO_2R^9$, $NR^{10}R^{11}$, $I^+R^{13}$ or $(R^{14-})I^+R^{13}$. Herein, it is preferred that: $R^6$s each represent methyl or n-butyl; $R^7$ and $R^8$ may be the same or different and each represent hydrogen, methyl, ethyl, propyl, butyl, heptyl, trifluoromethyl, or an optionally substituted phenyl group, or are combined with N to form aziridine, azetidine, pyrrolidine, piperidine or homo-piperidine; $R^9$ represents methyl, ethyl, propyl, butyl, heptyl, trifluoromethyl, or an optionally substituted phenyl group; $R^{10}$ and $R^{11}$ may be the same or different and each represent methyl, ethyl, propyl, butyl, heptyl, trifluoromethyl, or an optionally substituted phenyl group, or are combined with N to form aziridine, azetidine, pyrrolidine, or piperidine; and $R^{13}$ represents a $C_{1-6}$-alkyl-substituted phenyl group, a $C_{1-6}$-alkoxy-substituted phenyl group, or a phenyl group, or represents a substituted or unsubstituted 5- to 7-membered heterocyclic group containing one or more from N, S or O atoms. Particularly preferred examples of the heterocyclic group include thienyl, furanyl, pyridinyl, piperidinyl, and piperazinyl groups. $R^{14}$ preferably represents a halogen, or a tetrafluborate, nitrate, triflate, sulfonyloxy, toluenesulfonyloxy or perchlorate group.

In the present compound, preferably, R represents $BR^3R^4$, $BX_3^-$ or $BX_3^-M^+$ wherein Xs each represent F, and $M^+$ represents an alkali metal ion or ammonium ion. $R^3$ and $R^4$ each represent OH, or are together combined with B to form a ring as a protecting group.

$R^1$ represents hydrogen, or a protecting group $PG^1$ for a carboxylic acid. $PG^1$ is not particularly limited, and denotes any protecting group known by those skilled in the art for a carboxylic acid. Examples thereof include protecting groups described in Greene Wuts, "Protective Groups in Organic Synthesis", $3^{rd}$ edition (a company, Wiley-Interscience in USA). Typically, the group concerned can be converted into an ester type to be protected, using ester condensation conditions or alkylation conditions. $PG^1$ is, for example, an alkyl group having 1 to 7 carbon atoms, or an aromatic group such as a benzyl group. Specific examples thereof include alkyl groups such as methyl, ethyl, n-propyl, iso-propyl, n-butyl, iso-butyl, sec-butyl, tert-butyl and n-pentyl groups, and aromatic groups such as benzyl, p-methoxybenzyl and p-nitrobenzyl groups. $PG^1$ is in particular preferably a tert-butyl or benzyl group, which is not easily affected by racemization when the protected group is de-protected.

$R^2$ is hydrogen, or a protecting group $PG^2$ for an amino group. The protecting group for an amino acid may be any protecting group known by those skilled in the art. Examples thereof include protecting groups described in Greene Wuts "Protective Groups in Organic Synthesis", $3^{rd}$ edition (the company Wiley-Interscience in USA). Preferred examples thereof include benzyloxycarbonyl, acetyl, trifluoroethylcarboxy, tert-butyloxycarbonyl, fluorenylmethyloxycarbonyl, trichloroethoxycarbonyl, trifluoroacetyl, allyloxycarbonyl, benzyl, propargyloxycarbonyl, benzoyl, phthaloyl, toluenesulfonyl, and nitrobenzenesulfonyl groups although the protecting group is not limited thereto. Of these examples, benzyloxycarbonyl and tert-butyloxycarbonyl groups are preferred, which can be subjected to de-protection in a short period.

When $R^3$ and $R^4$ are together combined with B (boron atom) to form a ring as a protecting group for B, $R^3$ and $R^4$ are each preferably a group that forms a saturated or unsaturated 3- to 10-membered ring which may be substituted. Examples of the structure of the ring herein also include spiro-rings and condensed rings. Examples of the group that can form the ring include pinacol, 2,2-dimethyl-1,3-propanediol, N-methyldiethanolamine, 1,8-diaminonaphthalene, N-methyliminodiacetic acid, 1,1,1-trishydroxymethylethane, and catechol although the group is not limited. The group is in particular preferably $O-R^5-O$ wherein $-R^5-$ represents an alkylene group that has 2 to 7 carbon atoms and may be substituted. Of these examples, pinacol is preferred. The alkylene group that may be substituted denotes a $C_{1-6}$-alkyl-group- or $C_{1-6}$-alkoxy-group-substituted alkylene.

In the present invention, the alkyl group having 1 to 7 carbon atoms is in particular preferably a methyl, ethyl, n-propyl, iso-propyl, n-butyl, iso-butyl, sec-butyl, tert-butyl, or n-pentyl group. The halogen-substituted alkyl group denotes an alkyl group having 1 to 7 carbon atoms wherein its hydrogen atom, or one or more of its hydrogen atoms are substituted with one or more halogens. The alkyl group is preferably a trifluoromethyl group although the group is not limited. The substituted phenyl group denotes a phenyl group, or a phenyl group having, at one to three positions thereof, one or more substituents independently of each other. The substituted 3- to 10-membered ring denotes a 3- to 10-membered ring, or a 3- to 10-membered ring having, at one to three positions thereof, one or more substituents independently of each other. The substituted heterocyclic group has a heterocycle, or a heterocyclic group having, at one to three positions of the heterocycle, one or more substituents independently of each other. Examples of the substituent(s) of the phenyl group, the 3- to 10-membered ring, or the heterocycle include $C_{1-6}$ alkyl, $C_{1-6}$ alkoxy, hydroxy, amino and nitro groups although the substituent(s) is/are not limited.

The BPA derivative of the present invention can be synthesized through, for example, a step A, B or C illustrated below.

Any protecting group used in reaction formulae illustrated below may be appropriately changed. The protecting group is not limited to any one of illustrated examples.

Step A:

[Formula 8]

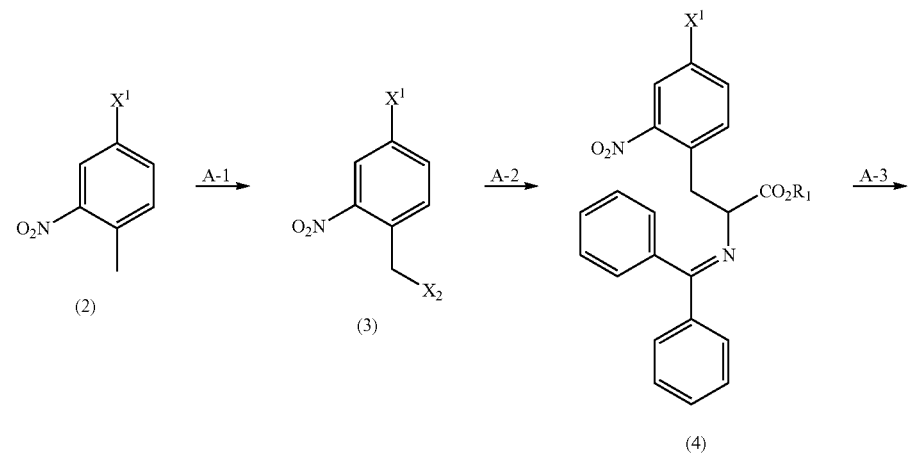

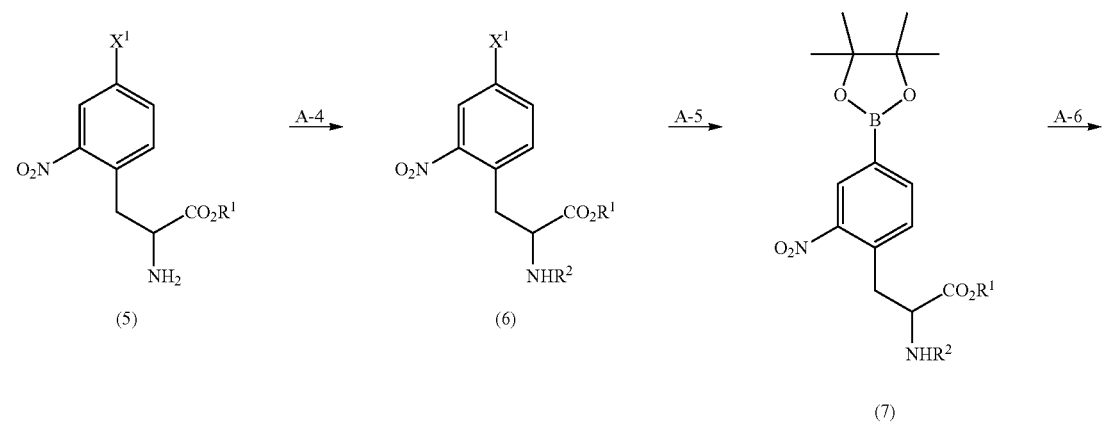

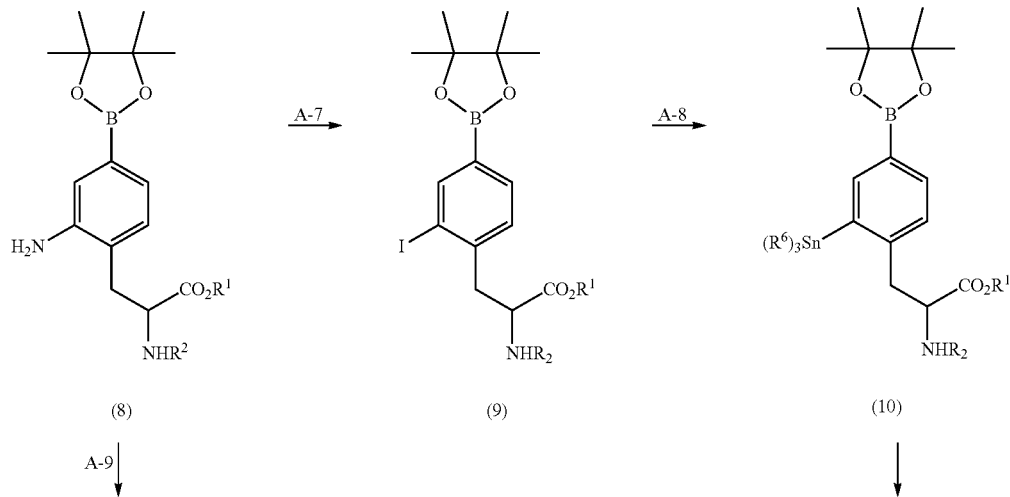

-continued
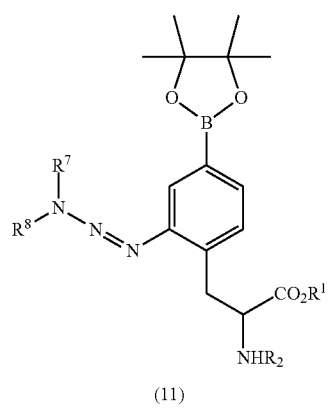
(11)
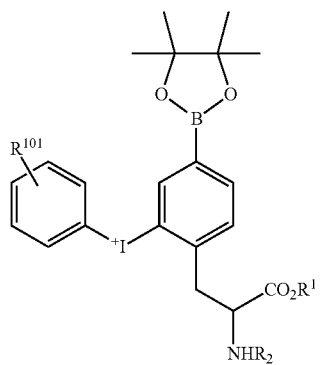
(101)
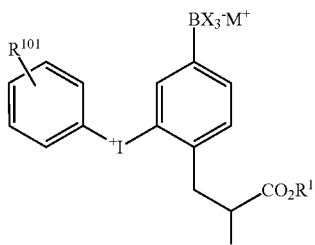
(102)
Step A:
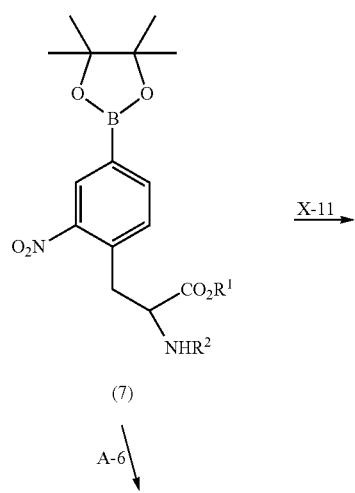 <span>—X-11→</span> 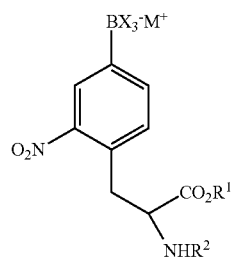
(7)          (104)
A-6
[Formula 9]

13
-continued
14
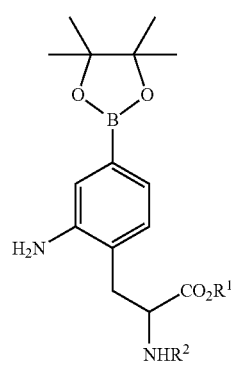
(8)
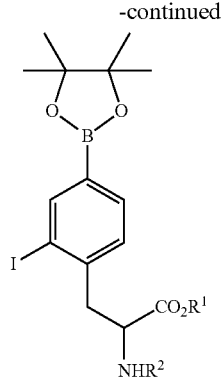
(9)
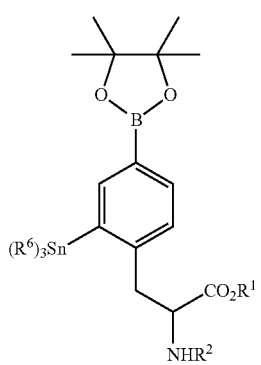
(10)
A-7 →   A-8 →
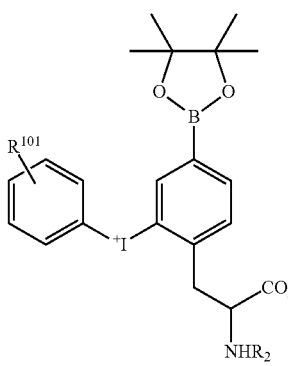
(101)
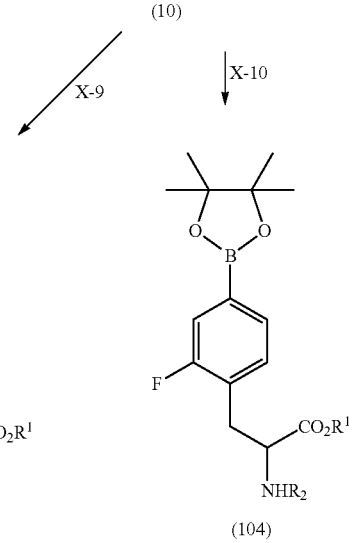
(104)
X-9 ↙   X-10 ↓
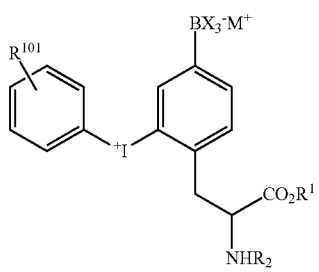
(102)
X-12 ↙
X-13 ↓
(103)

Step B:
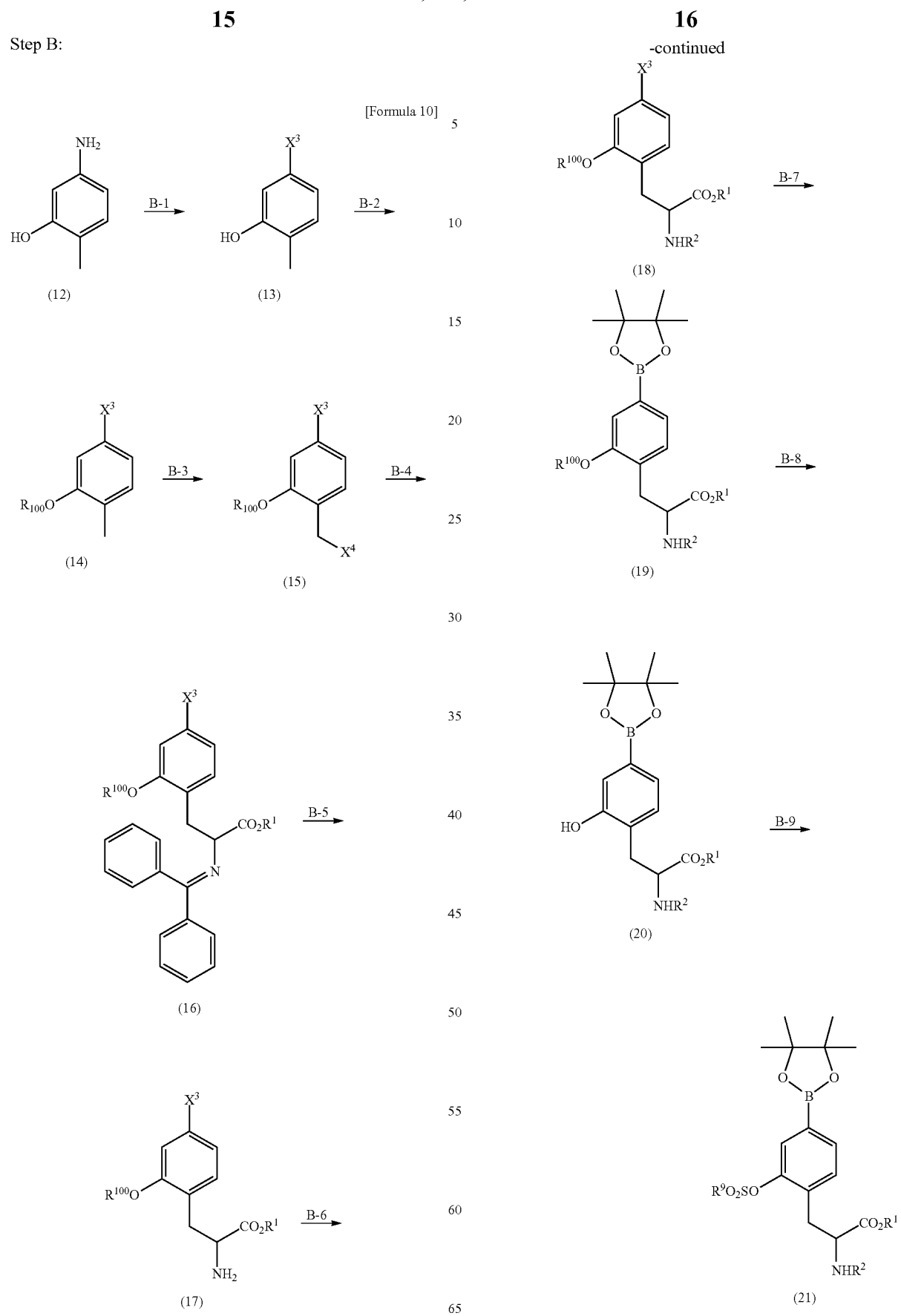

Step C:

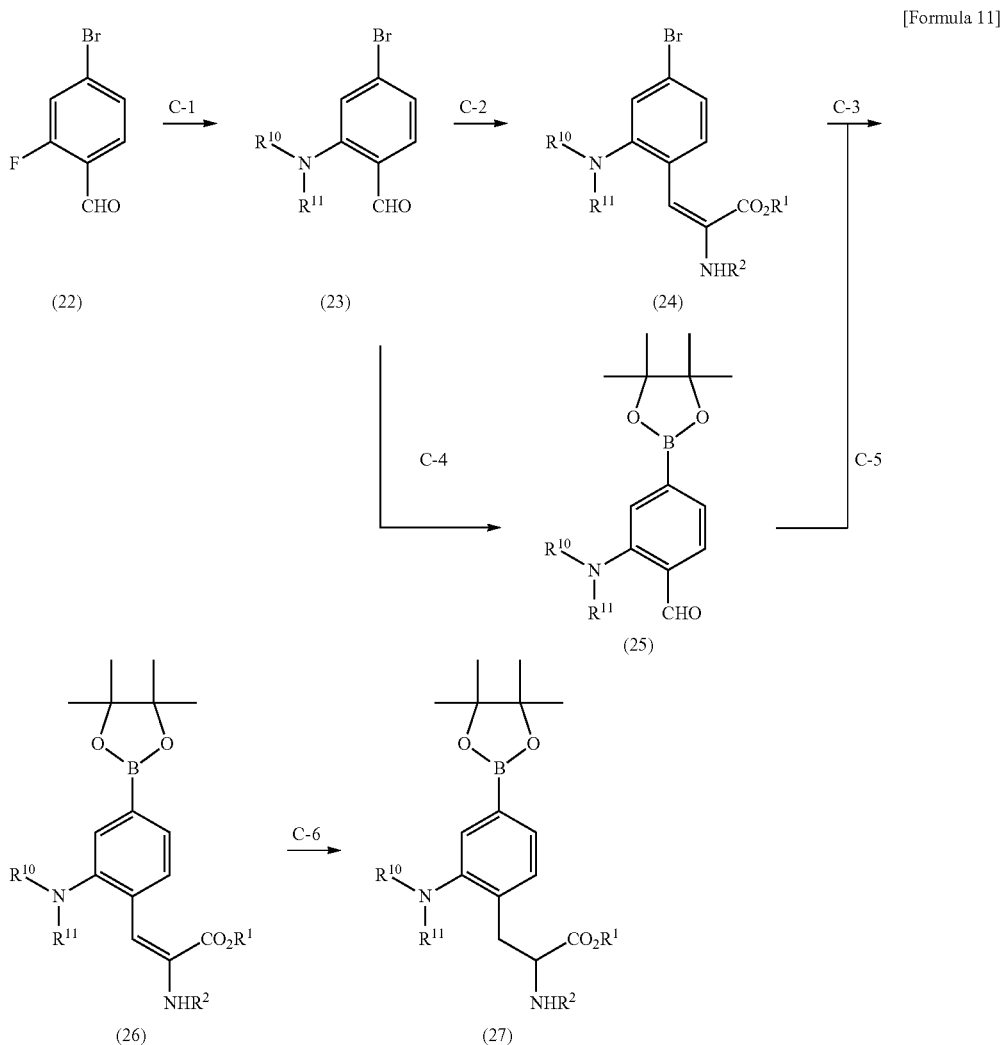

(22) (23) (24) (25) (26) (27)

[Formula 11]

In a reaction in each of steps A to C, the reaction temperature is varied in accordance with the solvent, the starting materials, the reagent(s) and others to be appropriately selected. The reaction period is varied in accordance with the solvent, the starting materials, the reagent(s), the reaction temperature and others to be appropriately selected.

In the reaction in each of the steps, the target compound in each step may be isolated from the reaction mixture by a routine procedure after the end of each reaction.

The target compound is obtained, for example, by (i) filtrating away the catalyst and other insoluble matters as required, (ii) adding, to the reaction mixture, water and a solvent immiscible with water (for example, ethyl acetate or chloroform) to extract the target compound, (iii) washing the organic phase with water, and optionally using a drying agent such as anhydrous magnesium sulfate to dry the phase, and (iv) distilling off the solvent. The resultant target compound may be further purified by a known method (such as silica gel column chromatography) as required. The target compound in each of the steps may be supplied for the next reaction without being purified.

In each of the steps, any one of the symbols has the same meaning as the definition made in the other description. $R^{100}$ represents an alkyl group such as methyl, ethyl, propyl, butyl, heptyl or trifluoromethyl, a halogen-substituted alkyl group, hydrogen, an optionally substituted phenyl group, or a protecting group for a phenolic OH, such as a substituted silyl group. $R^{101}$ represents a $C_{1-6}$ alkyl group, a $C_{1-6}$ alkoxy group, a hydroxy group, an amino group, or a nitro group.

Step A-1:

Step A-1 is specifically a step of causing a compound (2) to react with a halogenating reagent in the presence of a catalyst to produce a compound (3). The compound (2) is known, and is commercially available. The compound may be obtained by a synthesis from a commercially available compound.

$X^1$ and $X^2$ each independently represent a halogen, and each in particular preferably represent iodine or bromine. The symbols Xs are each preferably bromine from the viewpoint of the availability of the compound.

Examples of the used halogenating reagent include N-bromosuccinimide, dibromoisocyanuric acid, 1,3-diiodo-5,5'-dimethylhydantoin, and N-iodosuccinimide. The used catalyst is a radical polymerization agent such as a peroxide or AIBN.

A solvent to be used is not particularly limited. Examples thereof include benzene, chloroform, and carbon tetrachloride. Carbon tetrachloride is particularly preferred.

The reaction temperature is preferably from room temperature to 120° C., more preferably from 70 to 100° C.

The reaction period is preferably from 1 to 24 hours, more preferably from 6 to 18 hours.

Step A-2:

Step A-2 is a step of causing the compound (3) to react with an interlayer transfer catalyst and a modified amino acid that are generally used in Maruoka's reaction in the presence of a base to produce a compound (4).

The modified amino acid used in Maruoka's reaction is not limited. Preferred examples thereof include a methyl ester of N-diphenylmethyleneglycine, an ethyl ester of N-diphenylmethyleneglycine, a t-butyl ester of N-diphenylmethyleneglycine N-diphenylmethyleneglycine, a t-butyl ester of 4-chlorobenzylideneglycine, and a benzyl ester of N-diphenylmethyleneglycine. Of these examples, particularly preferred is a t-butyl ester of N-diphenylmethyleneglycine.

The used base is not limited. Preferred examples thereof include lithium hydroxide, sodium hydroxide, potassium hydroxide, and triethylamine. Potassium hydroxide is particularly preferred for the reaction rate.

Preferred examples of the modified amino acid used in Maruoka's reaction include O-allyl-N-(9-anthracenylmethyl)cinchonidinium bromide, and (S)-(+)-4,4-dibutyll-2,6-bis(3,4,5-trifluorophenyl)-4,5-dihydro-3H-dinaphth[7,6,1,2-cde]azemipium bromide.

Preferred examples of a solvent to be used include toluene, dichloromethane, and chloroform. Toluene is particularly preferred for the environment.

The reaction temperature is preferably from −20 to 100° C., more preferably from −4° C. to room temperature.

The reaction period is preferably from 30 minutes to 24 hours, more preferably from 1 to 18 hours.

The resultant compound may be purified; however, the compound may be shifted to the next step without being purified.

Step A-3:

Step A-3 is a step of putting the compound (4) to an acidic aqueous solution to remove its amino-group protector. A solvent to be used therefor may be citric acid, or a mixed solvent of an aqueous solution of oxalic acid, and acetone, acetonitrile, THF, DMF or DMSO. The solvent is more preferably citric acid, or a mixed solvent of an aqueous solution of oxalic acid, and acetone, acetonitrile or THF in order to be distilled off.

The reaction temperature is preferably from room temperature to 100° C., more preferably from room temperature to 80° C. The reaction period is preferably from 30 minutes to 24 hours, more preferably from 1 to 3 hours.

Step A-4:

Step A-4 is a step of using a protecting reagent for the compound (5) to protect its amino group under a basic condition. The used protecting reagent may be, for example, benzyl chloroformate, or di-t-butyl dicarbonate although the reagent is not limited.

Preferred examples of a base to be used include lithium hydroxide, sodium hydroxide, potassium hydroxide, sodium carbonate, potassium carbonate, and triethylamine although the base is not limited. Particularly preferred are sodium carbonate and potassium carbonate, which are mild.

A solvent to be used is desirably an amphipathic solvent. Examples thereof include acetone, acetonitrile, THF, DMF, and DMSO. The solvent is preferably acetone, acetonitrile or THF in order to be distilled off.

The reaction temperature is preferably from −20 to 100° C., more preferably from −4° C. to room temperature. The reaction period is preferably from 30 minutes to 24 hours, more preferably from 3 to 18 hours.

Step A-5:

Step A-5 is a step of using a pinacol boronation reagent to produce a pinacol borate derivative from the compound (6) in the presence of a palladium catalyst and a ligand. Examples of the used catalyst include palladium catalysts used generally in Suzuki-Miyaura coupling reactions, such as a palladium chloride cinnamyl complex, palladium acetate, and trisdibenzylideneacetone dipalladium although the catalyst is not limited to these compounds.

Examples of the ligand include phosphorus-containing ligands used generally in Suzuki-Miyaura coupling reactions, such as tricyclohexyl phosphine, 2-dicyclohexylphosphino-2,4,6-triisopropylbiphenyl, 2-dicyclohexylphosphino-2,-(N,N)-dimethylaminobiphenyl, 3,5-dimethoxy-2-dicyclohexylphosphino-2,4,6-triisopropylbiphenyl, and 3,5-dimethoxy-2-ditert-butylphosphino-2,4,6-triisopropylbiphenyl although the ligand is not limited to these compounds.

Examples of a base to be used include lithium hydroxide, sodium hydroxide, potassium hydroxide, sodium carbonate, potassium carbonate, and triethylamine, although not limited. Particularly preferred are sodium carbonate and potassium carbonate, which are mild.

A preferred solvent to be used is, for example, toluene or dioxane. The reaction temperature is preferably from room temperature to 150° C., more preferably from 80 to 120° C. The reaction period is preferably from 1 to 24 hours, more preferably from 2 to 18 hours.

Step A-6:

Step A-6 is a step of subjecting the compound (7) to hydrogenating reduction to produce an aniline derivative (8). A catalyst to be used therefor is, for example, palladium hydroxide, or palladium carbon although the catalyst is not limited.

Examples of a solvent to be used therefor include acetone, acetonitrile, THF, methanol, and ethanol. Preferred are methanol and ethanol, which are inactive for the reduction reaction.

The reaction temperature is preferably from −20 to 100° C., more preferably from room temperature to 50° C. The reaction period is preferably from 30 minutes to 24 hours, more preferably from 3 to 18 hours.

Step A-7:

Step A-7 is a step of producing, from the compound (8), a halogen derivative (9) via a diazonium. A reagent for the diazotization reaction may be, for example, sodium nitrite, potassium nitrite, or an alkyl nitrite such as isobutyl nitrite. The iodinating reagent may be, for example, sodium iodide, potassium iodide or iodine, which is known.

Examples of a solvent to be used include water, acetone, acetonitrile, THF, methanol, ethanol, and mixed solvents each composed of two or more of these solvents. Of these examples, acetone is preferred since this solvent is inactive to the diazotization reaction.

The reaction temperature is preferably from −20° C. to room temperature, more preferably from −10 to 5° C. The reaction period is preferably from 30 minutes to 2 hours, more preferably from 30 minutes to 1 hour.

Step A-8:

Step A-8 is a step of producing, from the compound (9), a trialkyltin compound (10) by a Suzuki-Miyaura coupling reaction. A reaction reagent therefor may be, for example, tributyltin, or trimethyltin. A catalyst to be used therefor may be a palladium catalyst used ordinarily for Suzuki-Miyaura coupling reactions, examples thereof including a palladium chloride cinnamyl complex, palladium acetate, trisdibenzylideneacetone dipalladium and tetrakistriphenylphenylphosphinopalladium, although the catalyst is not limited thereto. Of these examples, preferred is tetrakistriphenylphenylphosphinopalladium.

Examples of a base to be used include lithium hydroxide, sodium hydroxide, potassium hydroxide, sodium carbonate, potassium carbonate, sodium acetate, potassium acetate, and triethylamine. Preferred are sodium acetate and potassium acetate, which are milder.

A preferred solvent to be used is, for example, toluene or dioxane. The reaction temperature is preferably from room temperature to 150° C., more preferably from 80 to 120° C. The reaction period is preferably from 1 to 48 hours, more preferably from 2 to 24 hours.

Step A-9:

Step A-9 is a step of producing, from the compound (8), a triazene derivative (11) via a diazonium.

A reaction reagent for the diazotization may be, for example, sodium nitrite, potassium nitrite, or an alkyl nitrite such as isobutyl nitrite. The reaction reagent may be, for example, dimethylamine, cyclopentylamine or cyclohexylamine, which is known.

Examples of a solvent to be used include water, acetone, acetonitrile, THF, methanol, ethanol, and mixed solvents each composed of two or more of these solvents. Of these examples, acetone is preferred since this solvent is inactive to the diazotization reaction.

The reaction temperature is preferably from −20° C. to room temperature, more preferably from −10 to 5° C. The reaction period is preferably from 30 minutes to 2 hours, more preferably from 30 minutes to 1 hour.

For step X-9 for converting the compound (10) to a compound (101), the following operation is given as an example although an operation therefor is not limited:

The compound (10) is dissolved into a solvent, and thereto is then added an iodonium, such as Koser's reagent, under a nitrogen gas flow.

Examples of the used solvent include water, dichloromethane, acetone, acetonitrile, THF, methanol, ethanol, trifluoroethanol, and mixed solvents each composed of two or more of these solvents. Of these examples, dichloromethane is preferred.

The reaction temperature is preferably from −20° C. to room temperature, more preferably from −10 to 5° C. The reaction period is preferably from 30 minutes to 2 hours.

A reagent used in step X-12 for converting the compound (101) to a compound (102) may be a hydrogen halide such as hydrogen fluoride or hydrogen chloride.

Examples of a solvent to be used therefor include water, dichloromethane, acetone, acetonitrile, THF, methanol, ethanol, and mixed solvents each composed of two or more of these solvents. Of these examples, preferred is a combination of water with dichloromethane.

The reaction temperature is preferably from 0 to 60° C., more preferably room temperature (a temperature from 20 to 30° C.). The reaction period is preferably from 30 minutes to 24 hours, more preferably from 1 to 12 hours.

A reagent used in step X-13 for converting the compound (102) to a compound (103) may be hydrogen fluoride.

Examples of a solvent to be used include water, dichloromethane, acetone, acetonitrile, THF, methanol, ethanol, DMF, DMSO, and mixed solvents each composed of two or more of these solvents. Of these examples, preferred is dichloromethane alone, or a combination thereof with acetonitrile, DMF or DMSO.

The reaction temperature is preferably from −20 to 180° C., more preferably from 80 to 160° C. The reaction period is preferably from 5 minutes to 2 hours, more preferably from 10 minutes to 1 hour.

Step X-10 for Converting the Compound (10) to a Compound (104):

A reagent therefor may be an alkali fluoride.

Examples of a solvent to be used therefor include water, dichloromethane, acetone, acetonitrile, THF, methanol, ethanol, and mixed solvents each composed of two or more of these solvents. Of these examples, preferred is dichloromethane alone, or a combination of water with dichloromethane.

The reaction temperature is preferably from −20° C. to room temperature, more preferably from −10 to 5° C. The reaction period is preferably from 30 minutes to 2 hours, more preferably from 30 minutes to 1 hour.

Step X-11 for Converting the Compound (7) to the Compound (104):

A reagent therefor may be an alkali halide.

Examples of a solvent to be used therefor include water, dichloromethane, acetone, acetonitrile, THF, methanol, ethanol, and mixed solvents each composed of two or more of these solvents. Of these examples, preferred is dichloromethane alone, or a combination of water with dichloromethane.

The reaction temperature is preferably from 0 to 60° C., more preferably room temperature (a temperature from 20 to 30° C.). The reaction period is preferably from 30 minutes to 2 hours, more preferably from 30 minutes to 1 hour.

Step B-1:

Step B-1 is a step of producing, from the known compound (12), a halogen derivative (13) via a diazonium.

A reaction reagent for the diazotization may be, for example, sodium nitrite, potassium nitrite, or an alkyl nitrite such as isobutyl nitrite.

$X^3$ represents a halogen, particularly, iodine, bromine or chlorine. A reagent for the halogenation may be, for example, a Sandmeyer reagent, or sodium iodide, potassium iodide or iodine, which is known. Of these examples, suitable is copper bromide, which is a stable Sandmeyer reagent. Examples of a solvent to be used include water, acetone, acetonitrile, THF, methanol, ethanol, and mixed solvents each composed of two or more of these solvents. Of these examples, acetone is preferred since this solvent is inactive to the diazotization reaction. The reaction temperature is preferably from −20° C. to room temperature, more preferably from −10 to 5° C. The reaction period is preferably from 30 minutes to 2 hours, more preferably from 30 minutes to 1 hour.

Step B-2:

Step B-2 is a step of producing a compound (14) yielded by protecting the hydroxy group of the compound (13).

Examples of a protecting group therefor include methyl, benzyl, methoxybenzyl, tert-butyl, methoxymethyl, 2-tetrahydropyranyl, ethoxyethyl, acetyl, pivaloyl, benzoyl, trimethylsilyl, triethylsilyl, tert-butyldimethylsilyl, triisopropylsilyl, and tert-butyldiphenylsilyl groups although the group is not limited.

Examples of a solvent to be used therefor include mixed solvents each composed of water with acetone, acetonitrile, THF, methanol or ethanol. Of these examples, acetone is preferred since this solvent is inactive to diazotization reaction.

The reaction temperature is preferably from −20° C. to room temperature, more preferably from −10 to 5° C.

The reaction period is preferably from 30 minutes to 2 hours, more preferably from 30 minutes to 1 hour.

Step B-3

Step B-3 is a step of producing a compound (15) yielded by halogenating the benzyl position of the compound (14) appropriately.

A reagent, conditions and others for the reaction are the same as in step A-1 described above.

Step B-4

Step B-4 is a step of producing an amino acid derivative (16) yielded by causing the compound (15) to undergo Maruoka's reaction.

A reagent, conditions and others for the reaction are the same as in step A-2 described above.

Step B-5:

Step B-5 is a step of producing an amine derivative (17) yielded by subjecting the compound (16) to de-diphenylmethylation. A reagent, conditions and others for the reaction are the same as in step A-3.

Step B-6:

Step B-6 is a step of producing an amine derivative (18) yielded by introducing a protecting group into the compound (17). A reagent, conditions and others for the reaction are the same as in step A-4.

Step B-7:

Step B-7 is a step of producing a pinacol borate derivative (19) yielded by introducing a pinacol boride into the compound (18). A reagent, conditions and others for the reaction are the same as in step A-5.

Step B-8:

Step B-8 is a step of eliminating the protecting group for the hydroxyl group of the compound (19) to produce a phenol derivative (20). Examples of a reagent for the de-protection include a solution of citric acid in water; a solution of an oxalic acid in water; a solution of trifluoroacetic acid, hydrochloric acid or hydrobromic acid in an organic solvent such as methanol, ethanol, dioxane or ethyl acetate, or in water; acidic components such as sulfuric acid, methanesulfonic acid and trifluoromethanesulfonic acid; and fluoride ions.

Examples of a solvent to be used include water, acetone, acetonitrile, THF, methanol, ethanol, and mixed solvents each composed of two or more of these solvents. Of these examples, preferred is acetone, which is inactive to diazotization reactions.

The reaction temperature is preferably from −20° C. to room temperature, more preferably from −10 to 5° C. The reaction period is preferably from 30 minutes to 2 hours, more preferably from 30 minutes to 1 hour.

The resultant compound can easily be purified through silica gel column chromatography.

Step B-9:

Step B-9 is a step of producing, from the phenol derivative (20), an alkyl- or allyl-sulfonyloxy derivative (21).

Examples of a reaction reagent therefor include methylsulfonyl chloride, trifluoromethanesulfonyl chloride, and p-toluenesulfonyl chloride.

Examples of a solvent to be used therefor include ether solvents such as dioxane and THF, and dichloromethane.

The reaction temperature is preferably from −20 to 100° C., more preferably from −10° C. to room temperature. The reaction period is preferably from 30 minutes to 2 hours, more preferably from 30 minutes to 1 hour.

The resultant compound can easily be purified through silica gel column chromatography.

Step C-1:

Step C-1 is specifically a step of causing fluorine of a known compound (22) to react with a secondary amine to produce a tertiary amine derivative. Examples of the reaction reagent include dimethylamine, diethylamine, aziridine, azetidine, pyrrolidine, and piperidine although the reagent is not limited to these compounds.

Examples of a solvent to be used therefor include ether solvents such as dioxane and THF, and dichloromethane.

The reaction temperature is preferably from room temperature to 100° C., more preferably from room temperature to 80° C.

The reaction period is preferably from 30 minutes to 24 hours, more preferably from 1 to 6 hours.

Step C-2:

Step C-2 is a step of causing a Wittig reagent to react with the compound (23) to produce an olefin (24).

Examples of the reaction reagent include [2-(1,3-dioxolane-2-yl)ethyl]triphenylphosphonium bromide, (1,3-dioxolane-2-yl-methyl)triphenylphosphonium bromide, (methoxymethyl)triphenylphosphonium chloride, (bromomethyl) triphenylphosphonium bromide, isoamyltriphenylphosphonium bromide, alkyl esters of any alkylphosphonoacetic acid, such as methyl dimethylphosphonoacetate and ethyl dimethylphosphonoacetate, and a benzyl ester or substituted benzyl esters of any dialkylphosphonoacetic acid.

Examples of a solvent to be used include ether solvents such as dioxane and THF, and dichloromethane.

The reaction temperature is preferably from −78 to 100° C., more preferably from −20 to 100° C. The reaction period is preferably from 30 minutes to 24 hours, more preferably from 1 to 6 hours.

Step C-3:

Step C-3 is a step of producing a pinacol borate derivative (26) yielded by introducing a pinacol boride into the compound (24).

A reagent, conditions and others for the reaction are the same as in step A-5 described above.

Step C-4:

Step C-4 is a step of producing a pinacol borate derivative (25) yielded by introducing a pinacol boride into the compound (23). A reagent, conditions and others for the reaction are the same as in step A-5 described above.

Step C-5:

Step C-5 is a step of causing a Wittig reagent to react with the compound (25) to produce an olefin (26). A reagent, conditions and others for the reaction are the same as in step C-2 described above.

Step C-6:

Step C-6 is a step of subjecting the compound (26) to reducing hydrogenation to produce a (27). A reagent, conditions and others for the reaction are the same as in step C-2 described above.

Examples of a reaction catalyst therefor include palladium catalysts such as palladium hydroxide and palladium-carbon, and ruthenium complexes.

Examples of a solvent to be used include ether solvents such as dioxane and THF, and alcohol solvents such as methyl alcohol.

The reaction temperature is preferably from −20 to 100° C., more preferably from room temperature to 80° C. The reaction period is preferably from 30 minutes to 120 hours, more preferably from 1 to 24 hours.

By substituting the thus-obtained BPA derivative of the present invention further with fluorine, a $^{18}$F-labeled BPA can be produced.

For example, accelerated protons are radiated to $H_2{}^{18}O$ to synthesize $H^{18}F$-hydrofluoric acid through $^{18}O$ (p,n) reaction, and then this acid is passed through an ion exchange resin column to be adsorbed thereon to separate this acid from $H_2{}^{18}O$, which is a non-adsorbed raw material. This column is subjected to elution-out into a solution of $K_2CO_3$ in water to yield $K^{+18}F^{-}$, which can be used as a nucleophilic agent.

[Formula 12]

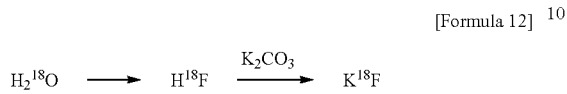

When Y is $NO_2$ or $N=N-NR^7R^8$ in the BPA derivative of the present invention, the derivative is labeled with $^{18}F$ by a known method. Specifically, the resultant $^{18}F$ anions are used as a nucleophilic agent and the anions are heated together with a phase transfer catalyst in an organic solvent, thereby yielding a labeled body. When Y is $NR^{10}R^{11}$, the BPA derivative is once caused to react with methyl iodide or the like to produce a quaternary amine and then a target compound is yielded therefrom by a known method.

When Y is $NH_2$, the BPA derivative is caused to react, via its diazonium salt, with $H^{18}F$ to label the derivative. When Y is I or $OSO_2R^9$, a labeled body of the BPA derivative is yielded by a known method. The labeled body can be obtained in a short period by Donalds' method (Non-Patent Document: Science, 325, 1661, 2009). Specifically, the labeled body is yielded in a short period by causing the BPA derivative to react with a nucleophilic agent $^{18}F^{-}$ in the presence of a palladium catalyst, and a ligand such as 2-dicyclohexylphosphino-2,4,6-triisopropylbiphenyl (Reference Example 1).

Furthermore, when Y is $Sn(R^6)_3$, a labeled body of the BPA derivative is yielded by Ermerts' method (Non-Patent Document: J. Label. Compd. Radiopharm., 47, 429, 2004). Specifically, the labeled body is yielded preferably from the viewpoint of efficiency by causing the BPA derivative to react with a hydroxyl(tosyloxy)iodoarene, such as Koser's reagent, to produce a diallyliodonium salt once, and then causing this salt to react with a nucleophilic agent $^{18}F^{-}$ (Reference Example 2).

The present precursor is dissolved in an amount of 1 to 100 mg into a reaction solvent, and thereto are added a phase transfer catalyst, and a base as a trapping agent. This system is heated to synthesize a target compound. Thereto are added a catalyst and a ligand in accordance with the substituent of the precursor to conduct a reaction. Examples of the reaction solvent include chloroform, benzene, toluene, xylene, acetonitrile, tetrahydrofuran, dimethylsulfoxide, dimethylformamide, ethyl acetate, and acetone although the solvent is not limited to these solvents. Examples of the phase transfer catalyst include crown ethers, kryptofix, and salts each having a long chain alkyl ammonium cation, such as a tetrabutyl ammonium salt, a trioctylmethyl ammonium salt, and a benzyldimethyloctadecyl ammonium salt although the catalyst is not limited to these salts. Examples of the base as the trapping agent include potassium carbonate, cesium carbonate, sodium carbonate, and rubidium carbonate although the base is not limited to these compounds. The reaction temperature is from room temperature to the boiling point of the solvent, preferably from 60 to 180° C., more preferably from 90 to 160° C. However, in accordance with the substituent, the temperature has a preferred range not to be limited to this range.

The thus yielded $^{18}F$-labeled BPA denotes the following compound:

[Formula 13]

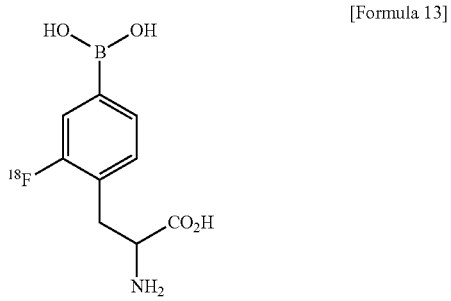 [SMILES: NC(Cc1ccc(B(O)O)cc1[18F])C(=O)O]

The use of the method of the present invention makes it possible to yield such a $^{18}F$-labeled BPA with a relatively high yield in a state with excellent specific activity thereof is good.

EXAMPLES

The present invention will be described in more detail by way of working examples described below. However, the invention is not limited to these examples.

In the examples, the following machine and reagents were used for analyzing any compound and isolating/purifying the compound: a machine, JNM-AL series AL400 manufactured by JEOL Ltd. at 400 MHz for NMR spectra.

Example 1

(1) Production of 4-bromo-1-(bromomethyl)-2-nitrobenzene

To carbon tetrachloride (100 mL) were added 2-nitro-6-bromotoluene (25.0 g, 116 mmol), N-bromosuccinimide (28.2 g, 162 mmol), and 2,2-azobis(2-methylpropionitrile) (1.90 mg, 11.6 mmol) to cause the reactants to react with each other for 18 hours while the reaction system was refluxed. Thereafter, the reaction liquid was filtrated, and the resultant filtrate was concentrated under a reduced pressure. The resultant was purified through silica gel column chromatography (AcOEt/n-hexane=1/9) to yield 18.5 g (54%) of the target compound. $^1$H-NMR (CDCl$_3$); 4.78 (s, 2H, CH$_2$), 7.46 (d, J=8.0, 1H, Ar), 7.74 (dd, J=2.0, 8.1, 1H, Ar), 8.18 (d, J=1.7, 1H, Ar).

(2) Production of (S)-tert-butyl 3-(4-bromo-2-nitro-phenyl)-2-(diphenylmethylene-amino)-propanoate To a two-phase mixed solution of a 9.0 M solution (100 mL) of potassium hydroxide and toluene (100 mL) were added N-(diphenylmethylene)glycinate (10.0 g, 33.9 mmol) and O-allyl-N-9-anthracenylmethylcinchonidium bromide (2.05 g, 3.39 mmol, 0.1 equivalent). This reaction system was cooled to 0° C., and then thereto was dropwise added a solution of the above-mentioned synthesized compound (10.0 g, 33.9 mmol) in toluene (30 mL). After the end of the addition, the system was stirred for 18 hours while kept as it was. Thereafter, the reaction solution was extracted with ether (50 mL) two times, and further the ether solution was washed with a saturated saline solution. The ether solution was then dried over magnesium sulfate, and concentrated under a reduced pressure to yield a crude target compound (17.6 g). This compound was subjected to the next step without being purified.

(3) Production of (S)-tert-butyl 2-amino-3-(4-bromo-2-nitrophenyl)propanoate The compound (17.6 g, 34.6 mmol) yielded through the previous steps was dissolved into THF (176 mL), and thereto was added a 30% solution (88 mL) of citric acid in water. This mixed solution was caused to undergo a reaction under reflux for 1 hour. After the end of the reaction, the reaction solution was washed with ether (80 mL), and then neutralized with potassium carbonate. Thereafter, the resultant was subjected to extraction with EtOAc (80 mL) two times, and the combined EtOAc phase was dried over magnesium sulfate and concentrated under a reduced pressure to yield a crude target compound (5.44 g). The yield thereof from the benzylbromide body was 47.0%. This compound was subjected to the next step without being purified. $^1$H-NMR (CDCl$_3$); 1.45 (s, 9H, t-Bu), 3.08 (dd, J=8.8, 13.6, 1H, CH$_2$-α), 3.29 (dd, J=5.6, 13.6, 1H, CH$_2$-β), 3.62 (dd, J=5.6, 8.5, 1H, CH), 7.31 (d, J=8.4, 1H, Ar), 7.66 (dd, J=2.0, 8.4, 1H, Ar), 8.10 (d, J=2.0, 1H, Ar).

(4) Production of (S)-tert-butyl 3-(4-bromo-2-nitrophenyl)-2-(tert-butoxycarbonyl-amino)-propanoate The compound' (2.72 g, 7.88 mmol) yielded through the previous steps was dissolved into acetone (27 mL), and thereto was added Boc$_2$O (2.06 g, 9.46 mmol). Thereafter, thereto was added a solution (1.25 g, 11.8 mmol) of sodium carbonate in water to cause the reactants to react with each other for 18 hours at room temperature. Thereafter, the reaction system was concentrated under a reduced pressure to distill off acetone. The residue was dissolved into AcOEt (40 mL). This solution was washed with a saturated saline solution, dried over magnesium sulfate, and then concentrated under a reduced pressure. Thereafter, the resultant was purified through a silica gel column (AcOEt/n-hexane: 1/7) to yield the target compound (2.80 g, 80%). $^1$H-NMR (CDCl$_3$); 1.75 (s, 12H), 1.44 (s, 9H, t-Bu), 3.08 (dd, J=8.0, 13.2, 1H, CH$_2$-α), 3.29 (dd, J=5.2, 13.5, 1H, CH$_2$-β), 4.54 (m, 1H, CH), 5.15 (d, J=8.0, 1H, NH), 7.29 (d, J=8.4, 1H, Ar), 7.65 (dd, J=1.7, 8.0, 1H, Ar), 8.11 (d, J=1.7, 1H, Ar).

(5) Production of (S)-tert-butyl 2-(tert-butoxycarbonylamino)-3-(2-nitro-4-(4,4,5,5-tetramethyl-1,3,2-dioxaborolane-2-yl)phenyl)propanoate Under a nitrogen gas flow, PdCl$_2$ (dba) (246 mg, 0.38 mmol) and tricyclophosphine (246 mg, 0.88 mmol) were suspended into dioxane (50 mL), and this suspension was stirred for 30 minutes. Thereafter, thereto were added bis(pinacolate)diborane (3.84 g, 13.8 mmol) and KOAc (1.86 g, 18.9 mmol), and further thereto was added the compound 3 (5.60 g, 12.6 mmol). Thereafter, the temperature of the system was raised to 100° C., and the system was stirred at this temperature under a nitrogen gas flow all night. Thereafter, the resultant was purified through a silica gel column (AcOEt/n-hexane=1/7) to yield the target compound (11.0 g, 87%). $^1$H-NMR (CDCl$_3$); 1.43 (s, 21H), 1.45 (s, 9H, t-Bu), 3.18 (dd, J=8.8, 13.6, 1H, CH$_2$-α), 3.52 (dd, J=5.2, 13.6, 1H, CH$_2$-β), 4.55 (m, 1H, CH), 5.15 (d, J=8.0, 1H, NH), 7.40 (d, J=7.6, 1H, Ar), 7.91 (dd, J=1.4, 7.6, 1H, Ar), 8.34 (d, J=1.2, 1H, Ar).

Example 2

(6) Production of (S)-tert-butyl 3-(2-amino-4-(4,4,5,5-tetramethyl-1,3,2-dioxaborolane-2-yl)phenyl)-2-(tert-butoxycarbonylamino)propanoate Into a flask for middle-pressure hydrogenation was put a mixture of a solution (20 mL) of the above-mentioned nitro compound (5.5 g, 11.2 mmol) in methanol, and 10% palladium carbon (0.55 g). Under a pressure (0.2 MPa) increased with hydrogen, the reaction system was stirred at room temperature for 18 hours. It was verified by TLC that the reaction advanced, and then the solvent was distilled off under a reduced pressure to yield a colorless oily amino compound (3.72 g, 72%). This compound was subjected to the next step without being purified. $^1$H-NMR (CDCl$_3$); 1.30-1.43 (m, 30H, pinacol (CH$_3$)$_4$, -Boc, -t-Bu) 2.89 (dd, J=8.0, 14.0, 1H, CH$_2$-α), 3.03 (dd, J=4.4, 14.0, 1H, CH$_2$-β) 4.36 (m, 1H, CH), 5.36 (d, J=7.2, 1H, NH), 6.96 (d, J=7.6, 1H, Ar), 7.09-7.11 (m, 2H, Ar), 8.34 (d, J=1.2, 1H, Ar).

Example 3

(7) Production of (S)-tert-butyl 2-(tert-butyloxycarbonylamino)-3-(2-iodo-4-(4,4,5,5-tetramethyl-1,3,2-dioxaborolane-2-yl)phenyl)propanoate To water (25 mL) was added 57% HI (5.0 g), and further thereto was added CuI(I) (480 mg, 2.52 mmol). Thereto was added a solution in which the above-mentioned amino body (2.50 g, 5.04 mmol) was dissolved in acetonitrile (25 mL). Thereto was dropwise and slowly added a solution (5 mL) of sodium nitrite (365 mg, 5.29 mmol) in water through a dropping funnel while the reaction system was cooled with ice. This system was stirred at 0° C. for 30 minutes, and then the system was further stirred at room temperature for 30 minutes. Thereafter, the system was subjected to extraction with ethyl acetate three times. The ethyl acetate phase was washed once with a saturated saline solution, dried over magnesium sulfate, and then concentrated under a reduced pressure. Thereafter, the resultant was purified through a silica gel column (AcOEt/n-hexane=1/9) to yield the target compound (1.40 g, 46%).
$^1$H-NMR (CDCl$_3$); 1.33 (s, 12H, pinacol (CH$_3$)$_4$), 1.37 (s, 9H, t-Bu), 1.43 (s, 9H, t-Bu), 2.97 (dd, J=9.2, 14.0, 1H, CH$_2$-α), 3.05 (dd, J=4.8, 13.6, 1H, CH$_2$-β), 4.50 (m, 1H, CH), 5.06 (d J=8.8, 1H, NH), 6.96 (d, J=8.0, 1H, Ar), 7.57 (dd, J=1.6, 8.0, 1H, Ar), 8.16 (d, J=1.6, 1H, Ar).

Example 4

(8) Production of (S)-tert-butyl 2-(tert-butyloxycarbonylamino)-3-(4-(4,4,5,5-tetramethyl-1,3,2-dioxaborolane-2-yl)-2-(tri-n-butylstannyl)phenyl)propanoate In an egg-plant shaped flask, the above-mentioned compound (371 mg, 0.705 mmol) was dissolved into toluene (30 mL) under an argon atmosphere. Thereto were added Pd(PPh)$_4$ and (SnBu$_3$)$_2$, and then the reaction system was heated and refluxed for 24 hours. The reaction solution was concentrated and purified through silica gel chromatography (n-hexane/AcOEt=19/1) to yield the target compound as a colorless oily substance (175 mg, 34%).
$^1$H-NMR (CDCl$_3$); 0.89 (t, J=7.6, 9H, —CH$_2$CH$_2$CH$_3$×3), 1.11 (m, 6H, —CH$_2$CH$_2$CH$_3$×3), 1.31-1.37 (m, 21H, —CH$_2$CH$_2$CH$_3$×3, pinacol-CH$_3$×4, t-Bu), 1.44 (s, 9H, t-Bu), 2.93

(dd, J=9.2, 14.4, 1H, $CH_2$-α), 3.05 (dd, J=4.4, 14.4, 1H, $CH_2$-β), 4.41 (m, 1H, CH), 4.73 (d, J=8.4, 1H, NH), 7.23 (d, J=7.6, 1H, Ar), 7.68 (dd, J=7.4, 1.2, 1H, Ar), 7.84 (m, J=1.2, 1H, Ar).

Example 5

Production of (S)-(2-(3-tert-butoxy-2-(tert-butoxycarbonylamino)-3-(oxopropyl)-5-(4,4,5,5-tetramethyl-1,3,2-dioxaborane-2-yl)phenyl)(3-methoxyphenyl)iodonium tosylate Trifluoroethanol (2 mL) was added to 168 mg (0.228 mmol) of the compound yielded in Example 4, and then the reaction system was stirred in an ice water bath under a nitrogen gas flow for 1 hour. Thereto was added 96.1 mg (0.228 mmol) of hydroxy(3-methoxyphenyl)iodonium tosylate while the reaction system was cooled with ice. The reaction system was then stirred in the ice water bath for 15 minutes. From the reaction mixed liquid, the solvent was distilled off at room temperature. Hexane (10 mL) was added to the resultant mixture, and the mixture was washed. The reaction system was subjected to decantation to remove the solution phase. The same operation was made two times to distill off the remaining solvent completely in the resultant mixture. In this way, 167 mg of the target compound was yielded (yield: 86%).

$^1$H-NMR (DMSO-$d_6$); 1.31 (s, 12H, pinacol-$CH_3$×4), 1.39 (s, 9H, t-Bu), 1.54 (s, 9H, t-Bu), 2.29 (s, 3H, TsOH—$CH_3$), 3.15 (dd, J=10.8, 14.8, 1H, $CH_2$-α), 3.19 (m, 1H, $CH_2$-β, overlapped with water), 3.80 (s, 3H, —$OCH_3$), 4.18 (m, 1H, CH), 7.12 (d, J=8.0, 2H, TsOH—Ar), 7.22 (dd, J=2.8, 8.8, 1H, Ar), 7.11-7.47 (m, 2H, Ar), 7.47 (d, J=8.0, 2H, TsOH—Ar), 7.60-7.71 (m, 2H, Ar), 7.83-7.87 (m, 3H, Ar).

Example 6

Production of (S) (S)-tert-butyl 2-(tert-butyloxycarbonylamino)-3-(2-nitro-4-(potassiumtrifluoroborylphenyl)propanoate The compound 7 (104 mg, 0.211 mmol) was dissolved into MeCN (2 mL), and to this solution was added a solution (200 μL) of KF (49 mg, 0.844 mmol) in water. This system was stirred until the substrate was completely dissolved. Next, L-tartaric acid (65 mg, 0.433 mmol) was dissolved in THF (1 mL), and this was dropwise added to the reaction solution. The resultant system was stirred for 30 minutes. Thereafter, while the system was washed with MeCN, the resultant precipitation was filtered. The resultant filtrate was completely concentrated to yield the target compound as a palely yellow oily substance (78.2 mg, 78%).

$^1$H-NMR (CDCl$_3$); 1.35 (s, 9H, t-Bu), 3.00 (dd, J=9.6, 13.6, 1H, $CH_2$-α), 3.27 (dd, J=5.6, 14.0, 1H, $CH_2$-β), 4.22 (m, 1H, CH), 5.53 (d, J=8.0, 1H, NH), 7.13 (d, J=7.2, 6H, Ar), 7.57 (dd, J=1.2, 7.6, 1H, Ar), 7.86 (d, J=1.2, 1H, Ar).

Example 7

Production of (S)-(2-(3-tert-butoxy-2-tert-butoxycarbonylamino)-3-oxopropyl-5-(potassiumtrifluoroborylphenyl)(3-methoxyphenyl)iodonium tosylate The compound 101 (79 mg, 0.093 mmol) was dissolved into MeCN (1 mL), and to this solution was added a solution (100 μL) of KF (22 mg, 0.372 mmol) in water. This system was stirred. Next, L-tartaric acid (28 mg, 0.186 mmol) was dissolved in THF (0.5 mL), and this was dropwise added to the reaction solution. The resultant system was stirred for 30 minutes. Thereafter, while the system was washed with MeCN, the resultant precipitation was filtered. The resultant filtrate was completely concentrated, and then thereto was added Et2O (20 ml). This reaction system was then stirred all night. The resultant precipitation was collected by filtration. In this way, the target compound was yielded as a colorless crystal (35.1 mg, 45%).

$^1$H-NMR (DMSO-$d_6$); 1.31 (s, 9H, t-Bu), 1.44 (s, 9H, t-Bu), 2.29 (s, 3H, TsOH-$CH_3$), 3.06 (dd, J=9.6, 14.8, 1H, $CH_2$-α), 3.20 (m, 1H, $CH_2$-β, overlapped with water), 3.78 (s, 3H, —$OCH_3$), 4.13 (m, 1H, CH), 7.11 (d, J=8.0, 2H, TsOH-Ar), 7.19 (dd, J=2.8, 8.8, 1H, Ar), 7.34-7.49 (m, 3H, Ar), 7.48 (d, J=8.0, 2H, TsOH-Ar), 7.59-7.74 (m, 2H, Ar), 8.21 (m, 1H, Ar).

Example 8

(9) Production of (S)-tert-butyl 2-(tert-butoxycarbonylamino)-3-(2-nitro-4-potassiumtrifluoroborylphenyl)propanoate In the usual way, a protecting group was introduced into FBPA. $^1$H-NMR (CDCl$_3$); 1.33 (s, 9H, -Boc), 1.40 (s, 21H, t-Bu, pinacol $(CH_3)_4$), 3.06 (dd, J=8.8, 13.6, 1H, $CH_2$-α), 3.16 (dd, J=5.2, 13.6, 1H, $CH_2$-β), 4.45 (m, 1H, CH), 5.04 (d, J=8.0, 1H, NH), 7.20 (m, 1H, Ar), 7.42-7.50 (m, 2H, Ar).

Example 9

The compound of Example 1 and that of Example 3 are each used to make a test for checking whether substitution with fluorine was actually attained.

Reference Example 1

Fluorine-Labeling Reaction Using a Fluorine Substitution Reaction of an Iodo-Compound The compound (0.10 mmol) yielded in Example 1 is dissolved in toluene, and thereto are added a palladium chloride cinnamyl complex (5.0% by mol) and 2-dicyclohexylphosphino-2,4,6-triisopropylbiphenyl (6.0% by mol) under a nitrogen gas flow. Thereafter, a fluorinating reagent is added thereto to cause the reactants to react with each other at 100° C. under a nitrogen gas flow for 1 hour. The resultant fluorine-labeled compound is subjected to HPLC analysis.

Reference Example 2

Fluorine-Labeling Reaction Via a Diallyliodonium Salt

The compound (2.0 mmol) yielded in Example 3 is dissolved in dichloromethane, and then thereto is added Koser's reagent (0.81 g, 2.0 mmol) under a nitrogen gas flow. At room temperature, the reaction system is stirred for 2 hours, and the solvent is distilled off under a reduced pressure. The residue is solidified with diethyl ether, and this solid is supplied to the next step without being purified. Thereto is added a fluorinating reagent under a nitrogen gas flow to cause the reactants to react with each other at 80° C. The resultant fluorine-labeled compound is subjected to HPLC analysis.

Reference Example 3

Fluorine-Labeling Reaction Via a Potassium Trifluoro-Substituted Compound

The compound (2.0 mmol) yielded in Example 5 is dissolved in DMF, and then thereto is added a fluorinating reagent under a nitrogen gas flow to cause the reactants to react with each other at 80° C. The resultant fluorine-labeled compound is subjected to HPLC analysis.

The invention claimed is:

1. A compound represented by the following formula:

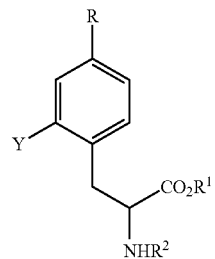

where R represents $BR^3R^4$, $BX_3^-$, or $BX_3^-M^+$ (X represents halogen; $M^+$ represents monovalent monoatomic cation, polyatomic cation, or complex cation); $R^1$ represents hydrogen or protecting group $PG^1$; $R^2$ represents hydrogen or protecting group $PG^2$; $R^3$ and $R^4$ each represents OH, or else $R^3$ and $R^4$ both combine with B (boron atom), to form a ring serving as protecting group for B, wherein the ring is selected from the group consisting of pinacol, 3,3-dimethyl-1,3-propanediol, N-methyldiethanolamine, 1,8-diaminonaphthalene, N-methyliminodiacetic acid, 1,1,1-trishydroxymethylethane, and catechol; Y represents F, or Br, $NO_2$, $NH_2$, $Sn(R^6)_3$, $N=N-NR^7R^8$, $OSO_2R^9$, $NR^{10}R^{11}$, substituted or unsubstituted phenyl iodo group, or substituted or unsubstituted heterocyclic iodo group; $R^6$ represents alkyl group having 1 to 7 carbon atoms; $R^7$ and $R^8$, may be the same or different, each represents hydrogen, alkyl group having 1 to 7 carbon atoms, halogen-substituted alkyl group having 1 to 7 carbon atoms, or optionally substituted phenyl group, or else $R^7$ and $R^8$ combine with N to form a 3- to 7-membered cyclic structure; $R^9$ represents alkyl group having 1 to 7 carbon atoms, halogen-substituted alkyl group having 1 to 7 carbon atoms, or optionally substituted phenyl group; and $R^{10}$ and $R^{11}$, which may be the same or different, each represents alkyl group having 1 to 7 carbon atoms, halogen-substituted alkyl group having 1 to 7 carbon atoms, or optionally substituted phenyl group, or else $R^{10}$ and $R^{11}$ combine with N to form a 3- to 7-membered cyclic structure; except that excluded here from is a situation in which the following conditions simultaneously exist: Y is F, $R^1$ and $R^2$ both represent hydrogen, and $R^3$ and $R^4$ both represent OH.

2. The compound according to claim 1, wherein Y represents F, $NO_2$, $NH_2$, $Sn(R^6)_3$, $N=N-NR^7R^8$, $OSO_2R^9$, $NR^{10}R^{11}$, $I^+R^{13}$, or $(R^{14})^-I^+R^{13}$ wherein: $R^6$ represents methyl or n-butyl; $R^7$ and $R^8$ may be the same or different, and each represent hydrogen, methyl, ethyl, propyl, butyl, heptyl, trifluoromethyl or an optionally substituted phenyl group, or $R^7$ and $R^8$ are combined with N to form aziridine, azetidine, pyrrolidine or piperidine; $R^9$ represents methyl, ethyl, propyl, butyl, heptyl, trifluoromethyl or an optionally substituted phenyl group; $R^{10}$ and $R^{11}$ may be the same or different, and each represent methyl, ethyl, propyl, butyl, heptyl, trifluoromethyl or an optionally substituted phenyl group, or $R^{10}$ and $R^{11}$ are combined with N to form aziridine, azetidine, pyrrolidine or piperidine; $R^{13}$ represents a $C_{1-6}$-alkyl-substituted phenyl group, a $C_{1-6}$ alkoxy substituted phenyl group or a phenyl group, or a 5- to 7-membered heterocyclic group having one or more atoms of N, S or O atoms; and $R^{14}$ represents a halogen, or a tetrafluoroborate, nitrate, triflate, sulfonyloxy, toluenesulfonyloxy, or perchlorate group.

3. The compound according to claim 1, wherein R represents $BR^3R^4$ wherein $R^3$ and $R^4$ each represent OH, or $R^3$ and $R^4$ are together combined with B (boron atom) to form the ring as the protecting group for B wherein the ring is selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol; or R represents $BX_3^-$ or $BX_3M$ wherein X represents F, and $M^+$ represents an alkali metal ion, an ammonium ion, a tetraalkylammonium ion, a tetraarylammonium ion, a tetraalkylphosphonium ion, a tetraarylphosphonium ion, or an imidazolium ion.

4. The compound according to claim 1, which is selected from the group consisting of:
tert-butyl 2-(tert-butoxycarbonylamino)-3-(2-nitro-4-(4,4,5,5-tetramethyl-1,3,2-dioxaborolane-2-yl)phenyl)propanoate;
tert-butyl 3-(2-amino-4-(4,4,5,5-tetramethyl-1,3,2-dioxaborolane-2-yl)phenyl)-2-(tert-butoxycarbonylamino)propanoate;
tert-butyl 2-(tert-butyloxycarbonylamino)-3-(2-iodo-4-(4,4,5,5-tetramethyl-1,3,2-dioxaborolane-2-yl)phenyl)propanoate;
tert-butyl 2-(tert-butyloxycarbonylamino)-3-(4-(4,4,5,5-tetramethyl-1,3,2-dioxaborolane-2-yl)-2-(tri-n-butylstannyl)phenyl)propanoate;
tert-butyl 2-(tert-butoxycarbonylamino)-3-(2-fluoro-4-(4,4,5,5-tetramethyl-1,3,2-dioxaborolane-2-yl)phenyl)propanoate;
(2-(3-tert-butoxy-2-(tert-butoxycarbonylamino)-3-oxopropyl)-5-(4,4,5,5-tetramethyl-1,3,2-dioxaborane-2-yl)phenyl)(3-methoxyphenyl)iodonium tosylate;
tert-butyl 2-(tert-butyloxycarbonylamino)-3-(2-nitro-4-potassiumtrifluoroborylphenyl)propanoate; and
(2-(3-tert-butoxy-2-(tert-butoxycarbonylamino)-3-oxopropyl)-5-(potassiumtrifluoroborylphenyl)(3-methoxyphenyl)iodonium tosylate.

5. A compound represented by the following formula:

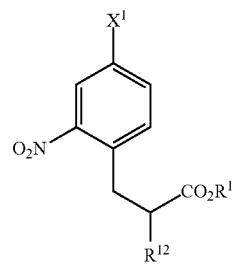

[Formula 6]

wherein $X^1$ represents a halogen; $R^1$ represents hydrogen or a protecting group $PG^1$; and $R^{12}$ represents $NHPG^2$ wherein $PG^2$ is a protecting group that is a n-propyl, iso-propyl, n-butyl, iso-butyl, sec-butyl, tert-butyl, n-pentyl, benzyl, p-methoxybenzyl, p-nitrobenzyl, benzyloxycarbonyl, acetyl, trifluoroethylcarboxy, tert-butyloxycarbonyl, fluorenylmethyloxycarbonyl, trichloroethoxycarbonyl, trifluoroacetyl, allyloxycarbonyl, propargyloxycarbonyl, benzoyl, phthaloyl, toluenesulfonyl, or nitrobenzenesulfonyl group, or $R^{12}$ represents aminomethylenediphenyl.

6. The compound according to claim 5, wherein $PG^2$ represents n-propyl, iso-propyl, n-butyl, iso-butyl, sec-butyl, tert-butyl, n-pentyl, benzyl, p-methoxybenzyl, or p-nitrobenzyl group.

7. The compound according to claim 5, wherein $PG^2$ represents benzyloxycarbonyl, acetyl, trifluoroethylcarboxy, tert-butyloxycarbonyl, fluorenylmethyloxycarbonyl, trichloroethoxycarbonyl, trifluoroacetyl, allyloxycarbonyl, propargyloxycarbonyl, benzoyl, phthaloyl, toluenesulfonyl, or nitrobenzenesulfonyl group.

\* \* \* \* \*